(12) United States Patent
Jakschies

(10) Patent No.: US 12,332,242 B2
(45) Date of Patent: Jun. 17, 2025

(54) METHOD AND DEVICE FOR DISCRIMINATING BETWEEN VIRAL AND BACTERIAL INFECTIONS

(71) Applicant: DEWACT LABS GMBH, Berlin-Charlottenburg (DE)

(72) Inventor: Detlef Jakschies, Hannover (DE)

(73) Assignee: DEWACT LABS GMBH, Berlin-Charlottenburg (DE)

( * ) Notice: Subject to any disclaimer, the term of this patent is extended or adjusted under 35 U.S.C. 154(b) by 29 days.

(21) Appl. No.: 17/897,026

(22) Filed: Aug. 26, 2022

(65) Prior Publication Data

US 2022/0404346 A1 Dec. 22, 2022

Related U.S. Application Data

(62) Division of application No. 16/766,337, filed as application No. PCT/EP2018/062466 on May 15, 2018, now abandoned.

(30) Foreign Application Priority Data

Nov. 22, 2017 (EP) ..................... 17203120

(51) Int. Cl.
*G01N 33/543* (2006.01)
*G01N 33/569* (2006.01)

(52) U.S. Cl.
CPC . *G01N 33/54388* (2021.08); *G01N 33/54306* (2013.01); *G01N 33/56911* (2013.01); *G01N 33/56983* (2013.01); *G01N 2333/4715* (2013.01); *G01N 2333/4737* (2013.01)

(58) Field of Classification Search
CPC .......... G01N 33/543; G01N 33/53; G01N 33/54306; G01N 33/56911; G01N 33/56983; G01N 2333/4515; G01N 2333/4737; G01N 33/54386; G01N 33/54388

See application file for complete search history.

(56) References Cited

U.S. PATENT DOCUMENTS

| | | |
|---|---|---|
| 5,466,581 A | 11/1995 | White et al. |
| 6,200,559 B1 | 3/2001 | Wussow |
| 6,924,153 B1 | 8/2005 | Boehringer et al. |
| 7,300,802 B2 | 11/2007 | Paek et al. |
| 2001/0007022 A1 | 7/2001 | Althaus et al. |
| 2003/0108550 A1 | 6/2003 | Althaus et al. |
| 2004/0214253 A1 | 10/2004 | Paek et al. |
| 2006/0292636 A1 | 12/2006 | Yarnall et al. |
| 2007/0196823 A1 | 8/2007 | Hansen et al. |
| 2010/0297611 A1 | 11/2010 | Sambursky et al. |
| 2013/0072580 A1* | 3/2013 | Barasch ............ G01N 33/6893 435/7.1 |
| 2015/0133412 A1 | 5/2015 | Isfort et al. |
| 2017/0114392 A1 | 4/2017 | Sambursky et al. |
| 2019/0180846 A1 | 6/2019 | Oved et al. |

FOREIGN PATENT DOCUMENTS

| | | |
|---|---|---|
| CN | 101541976 A | 9/2009 |
| CN | 105242049 A | 1/2016 |
| EP | 3489686 | 12/2020 |
| JP | 2016-509236 | 3/2016 |
| KR | 10-2005-0040866 A | 5/2005 |
| KR | 10-2015-0125002 | 11/2015 |
| WO | WO 1994/021280 | 9/1994 |
| WO | WO 2007/082259 | 7/2007 |
| WO | WO 2010/033963 | 3/2010 |
| WO | WO 2014/137858 | 9/2014 |
| WO | WO 2014/137860 | 9/2014 |
| WO | WO 2016/116181 | 7/2016 |

OTHER PUBLICATIONS

Delevoux et al., Can procalcitonin measurment help in differentiating between bacterial infection and other kinds of inflammatory processes, Ann Rheum Dis 2003; 62, pp. 337-340. (Year: 2003).*
Al-Masri et al., "Intracellular staining of Mx proteins in cells from peripheral blood, bone marrow and skin," Mol. Pathol., 50(1):9-14, 1997.
Cramer et al., "MxB is an interferon-induced restriction factor of human herpesviruses" Nature Communication, 9:1980, 2018.
Crameri et al., "mxB is an interferon-induced restriction factor of human herpesviruses," Swiss Society for Microbiology SSM Joint Annual Meeting, Abstract O57, 2017.
Decision to Grant European Patent issued in European Patent Application No. 17203120.5, dated Dec. 3, 2020.
Extended European Search Report issued in European Patent Application No. 17203120.5, dated Jan. 25, 2018.
Gao et al., "Structural basis of oligomerization in the stalk region of dynamin-like MxA," *Nature*, 465(7297):502-506, 2010.
Goujon et al., "Human MX2 is an interferon-induced post-entry inhibitor of HIV-1 infection," Nature, 502:559-562, 2013.
Haller et al., "Dynamins are forever: MxB inhibits HIV-1," *Cell Host Microbe.*, 14(4):371-373, 2013.
Jakschies et al., "Correlation of the antiproliferative effect and the Mx-homologous protein induction by IFN in patients with malignant melanoma," J. Invest. Dermatol., 95(Suppl. 6):238S-241S, 1990.
Jakschies et al., "Emergence and decay of the human Mx homolog in cancer patients during and after interferon-alpha therapy," J. Biol. Response Mod., 9(3):305-312, 1990.

(Continued)

*Primary Examiner* — Gary Counts
(74) *Attorney, Agent, or Firm* — Parker Highlander PLLC

(57) ABSTRACT

Provided herein is a point-of-care assay for detecting and differentiating between viral and bacterial infections, which effectively assists in the rapid differentiation of viral and bacterial infections. More particularly, an immunoassay that rapidly distinguishes between viral and/or bacterial infections is provided, wherein the viral marker is the interferon induced Mx-B protein and the bacterial markers are CRP/PCT/BPI.

9 Claims, 3 Drawing Sheets

(56) References Cited

OTHER PUBLICATIONS

Jakschies et al., "Strong transient expression of the type I interferon-induced MxA protein in hepatitis A but not in acute hepatitis B and C," *Heptaology*, 19(4):857-865, 1994.

Jakschies et al., "The human IFN-induced Mx-homologous proteins identified by 2D SDS-Page is specifically induced by type-I-interferons," *Proc. Int. Meeting on 2-D-Electrophoresis London*, 163:16.7-18.7, 1991.

Melen et al., "Human MxB protein, an interferon-alpha-inducible GTPase, contains a nuclear targeting signal and is localized in the heterochromatin region beneath the nuclear envelope," *J. Biol. Chem.*, 271(38):23478-23486, 1996.

Noe et al., "Clinical availability of serum procalcitonin in children with bacterial infection," Korean J. Pediatr. Infect. Dis., 17:108-113, 2010. (Korean language publication with English abstract).

Notice of Intent to Grant European Patent issued in European Patent Application No. 17203120.5, dated Jul. 13, 2020.

Office Communication issued in European Patent Application No. 17203120.5, dated Feb. 4, 2020.

PCT International Preliminary Report on Patentability issued in International Application No. PCT/EP2018/062466, dated May 26, 2020.

PCT International Search Report issued in International Application No. PCT/EP2018/062466, dated Jun. 15, 2018.

Rump et al., "Common variable immunodeficiency (CVID) and MxA-protein expression in blood leucocytes," *Clin. Exp. Immunol.*, 101(1):89-93, 1995.

Schultz & Weiss, "The bactericidal/permeability-increasing protein (BPI) in infection and inflammatory disease," Clin. Chim. Acta, 384:12-23, 2007.

Self et al., "Diagnostic Accuracy of FebriDx: A Rapid Test to Detect Immune Responses to Viral and Bacterial Upper Respiratory Infections," *J. Clin. Med.*, 6(10):94, 2017.

Towbin et al., "A whole blood immunoassay for the interferon-inducible human Mx protein," *J. Interferon Res.*, 12(2):67-74, 1992.

Von Wussow et al., "Effective natural interferon-alpha therapy in recombinant interferon-alpha-resistant patients with hairy cell leukemia," *Blood*, 78(1):38-43, 1991.

Von Wussow et al., "Humoral response to recombinant interferon-alpha 2b in patients receiving recombinant interferon-alpha 2b therapy," *J. Interferon Res.*, 9(Supp. 1):S25-31, 1989.

Von Wussow et al., "The human intracellular Mx-homologous protein is specifically induced by type I interferons," *Eur. J. Immunology*, 20(9):2015-2019, 1990.

Von Wussow et al., "The interferon-induced Mx-homologous protein in people with symptomatic HIV-1 infection," *AIDS*, 4(2):119-124, 1990.

Von Wussow et al., "Treatment of anti-recombinant interferon-alpha 2 antibody positive CML patients with natural interferon-alpha," *Br. J. Haemtaol.*, 78(2):210-216, 1991.

Wei et al., "Accumulation of MxB/Mx2-resistant HIV-1 Capsid Variants During Expansion of the HIV-1 Epidemic in Human Populations," *EBioMedicine*, 8:230-236, 2016.

\* cited by examiner

Fig. 2

|  | | Mx-pos.B | Mx-pos. + | CRP/PCT | BPI | Mx-A protein |
|---|---|---|---|---|---|---|
| VZV akut | 3 | 3 | 0 | 0 | 0 | 3 |
| VZV Zoster | 15 | 9 | 4 | 2 | 1 | 9 |
| EBV | 13 | 11 | 0 | 2 | 1 | 10 |
| CMV | 11 | 9 | 0 | 2 | 1 | 9 |
| Coxsackie | 6 | 6 | 0 | 1 | 0 | 4 |
| Influenza | 31 | 30 | 0 | 1 | 1 | 28 |
| Paramyxovirus | 21 | 18 | 2 | 2 | 0 | 17 |
| Togaviren | 20 | 8 | 10 | 1 | 0 | 12 |
| *Sum* | 120 | 94 | 16 | 11 | 4 | 92 |
| *Percent* | | | 92 | | 13 | 77 |
| Staphylokokken | 13 | 0 | 0 | 12 | 0 | |
| Streptokokken | 8 | 0 | 2 | 7 | 0 | |
| Tbc | 9 | 0 | 0 | 8 | 0 | |
| Pseudomonas | 4 | 1 | 0 | 1 | 1 | |
| Enterokokken | 3 | 0 | 0 | 3 | 0 | |
| E. Coli | 3 | 0 | 0 | 1 | 2 | |
| Klebsiellen | 1 | 0 | 0 | 1 | 1 | |
| Branhamella | 2 | 0 | 0 | 1 | 1 | |
| Borrelien | 2 | 0 | 0 | 2 | 0 | |
| Corynebak. | 3 | 0 | 1 | 2 | 0 | |
| Yersinien | 1 | 0 | 0 | 1 | 0 | |
| Lysterien | 1 | 1 | 0 | 1 | 0 | |
| *Sum* | 50 | 2 | 3 | 40 | 5 | |
| *Percent* | | | | 90 | | |

|  | Theoretical Hits | Calculated Hits | |
|---|---|---|---|
| viral | 50 | 46 | |
| bacteriell | 50 | 45 | |
| | | 91 | Hits between a viral and bacterial infection when both tests are performed together |

METHOD AND DEVICE FOR DISCRIMINATING BETWEEN VIRAL AND BACTERIAL INFECTIONS

This application is a division of U.S. application Ser. No. 16/766,337, filed May 22, 2020, now abandoned, which is a national phase application under 35 U.S.C. § 371 of International Application No. PCT/EP2018/062466, filed May 15, 2018, the entirety of each of which is incorporated herein by reference. International Application No. PCT/EP2018/062466, filed May 15, 2018, claims the benefit of European Patent Application No. 17203120.5, filed Nov. 22, 2017.

FIELD OF THE INVENTION

The present invention relates to the field of point of care assays (POC) for discriminating between viral and bacterial infections. More particularly, the invention pertains to an immunoassay that rapidly distinguishes between viral and/or bacterial infections.

BACKGROUND ART

Fever is a common cause of childhood visits to urgent care centers for both family practice and pediatric offices. Most commonly, this relates to either a respiratory infection or gastroenteritis. The high incidence of fever in children and the precautious administration of unnecessary antibiotics is reason to develop a rapid screening test for the biomarkers that indicate viral and/or bacterial infection.

Severe community-acquired pneumonia is caused by bacterial infections in around 60% of cases, requiring admission to an intensive care unit (ICU) for about 10% of patients. The remaining 40% are related to respiratory viruses. Most respiratory infections are related to pharyngitis of which 40% are caused by viruses and 25-50% by group A beta hemolytic streptococcus. The latter causes are acute bronchiolitis and pneumonia.

About 80% of all antimicrobials are prescribed in primary care, and up to 80% of these are for respiratory tract indications. Respiratory tract infections are by far the most common cause of cough in primary care. Broad spectrum antibiotics are often prescribed for cough, including acute bronchitis, and many of these prescriptions will benefit patients only marginally if at all, and may cause side effects and may promote antibiotic resistance. Factors that urge physicians to give antibiotics include the absence of an adequate diagnostic marker of bacterial infections, the concern about lack of patient follow-up, and the time pressure.

It is still challenging to differentiate quickly viral from bacterial infections. More recently, many new diagnostic markers have been identified. Several of these markers show great promise to differentiate viral from bacterial infections. Such proteins include the Mx-GTPases and the C-Reactive Protein (CRP).

Mx homologous proteins are members of the superfamily of high molecular weight GTPases. Accordingly, these GTPases are upregulated by type I alpha/beta or type II interferons (IFN). The Mx GTPases are expressed exclusively in IFN alpha/beta but not IFN gamma treated cells. Type I interferons play important roles in innate immune responses and have immunomodulatory, antiproliferative, and antiviral functions.

Own studies have shown that Mx-homologous human proteins have the following advantages: 1) The Mx-homologous human proteins in human are expressed mostly intracellular. They can be visible by intracellular staining in most cell compartiments [16]. 2) The Mx-homologous proteins are induced in a dose-dependent manner [6]. 3) The Mx-homologous human proteins are specifically induced by type-I-interferons, not by IFN-gamma, IL-I, TNF-alpha, or any of the other cytokines by bacterial infection [8,12]. 4) The Mx-homologous human proteins are much longer detectable in comparison with type-I-interferon in the peripheral blood system [6]. Therefore, these proteins are marker to identify viral diseases [7,14,15]. Furthermore, these proteins could be used as a marker to identify patients treated with type-I-interferons if the IFN-treatments are successful or not [5,9,10,11]. In early studies we detected these proteins by Western Blotting after SDS-PAGE.[12] But this procedure need more than two days. Therefore, we established an ELISA to detect these proteins within two days [13].

Based on these facts and on the assumption, that type-I-interferons remain within normal levels in patients with bacterial infections, the Mx-homologous protein expression in peripheral blood is a sensitive and specific marker for viral infection.

Similarly, most viral infections have been reported to cause little concentrations of acute phase response, and low C-reactive protein (CRP) concentrations, procalcitonin (PCT) levels and bactericidal/permeability-increasing protein (BPI). Therefore, these proteins will be used to distinguish illnesses of viral origin from those of bacterial etiology. Because the plasma concentration of CRP increases rapidly after stimulation and decreases rapidly with a short half-life, CRP can be a very useful tool in diagnosing and monitoring infections and inflammatory diseases. In Scandinavia, point of care CRP testing is part of the routine evaluation of patients with respiratory infections in general practice, and its use has proved cost-effective. In general practice, CRP is found valuable in the diagnosis of bacterial diseases and in the partial differentiation between bacterial and viral infections. Often the diagnostic value of CRP is found superior to that of the erythrocyte sedimentation rate (ESR) and superior or equal to that of the white blood cell count (WBC). The disadvantage of this point of care testing is the long detection time. These tests need between minimum 30 minutes and 2 hours.

Clinically, it can be challenging to differentiate certain systemic viral and bacterial infections. Bacterial cultures are usually performed in cases of severe infection such as pneumonia, or when the consequence of missing a diagnosis can lead to severe complications, such as with Strep throat. Often, cultures are difficult to obtain. Unfortunately, viral cultures are not routinely performed due to the significant time delay in receiving results. New viral screening PCR panels are useful, but they are expensive and do not provide information at the point of care, because the results can only be achieved after 24 hours. Thus, there remains a need for a simple, easy to use diagnostic test that is capable of differentiating viral and bacterial infections in short time!

WO2010/033963 discloses a lateral flow immunoassay for detection and differentiation between viral and bacterial infections. The bacterial marker is CRP and the viral marker is Mx-A-protein. The assay is marketed in Europe under the tradename FebriDx®. However, according to a study FebriDx® has only an accuracy of 63% and 84% for identifying bacterial and viral infections respectively[17]. Therefore, there is still the need for a rapid point of care diagnostic assay for more accurate and reliable discrimination between bacterial and viral infections in patients.

SUMMARY OF INVENTION

It is the object of the present invention to provide an improved and more accurate and specific diagnostic assay for reliable discrimination of bacterial and viral infections in patients in short time. The object is solved by the subject matter of the present invention.

According to the invention, there is provided a point-of-care (POC) immune assay device comprising:
a. a sample application zone, and
b. a detection zone with a first detection reagent with binding affinity to Mx-B-protein (Mx-B), and a second detection reagent with binding affinity to C-reactive Protein (CRP/PCT), and wherein the device is configured to detect Mx-B and CRP/PCT in a sample from a subject to discriminate between bacterial and viral infection.

According to a further embodiment of the invention, there is provided a point-of-care (POC) immune assay device comprising:
a. a sample application zone, and
b. a detection zone with a first detection reagent with binding affinity to Mx-B-protein (Mx-B), and a second detection reagent with binding affinity to C-reactive Protein (CRP), and a third detection reagent with binding affinity to procalcitonin (PCT) and/or fourth detection reagent with binding affinity to bactericidal/permeability-increasing protein BPI, and wherein the device is configured to detect Mx-B and CRP/PCT in a sample from a subject to discriminate between bacterial and viral infection.

One embodiment of the invention relates to the device as described herein, further comprising a third detection reagent with binding affinity to BPI.

One embodiment of the invention relates to device of as described herein, wherein said detection reagents are selected from synthetic molecules, nucleotides, nucleic acids, aptamers, peptides, proteins, enzymes, and antibodies.

One embodiment of the invention relates to the device as described herein, wherein said detection reagents are labelled with a detectable marker.

A further embodiment of the invention relates to device as described herein, wherein the detectable marker is selected from an enzyme label, fluorescent label, radiolabel, particulate label, colored latex particle, colored plastic particle, a colored phosphor particle, and a fluorescent particle.

A further embodiment of the invention relates to the device as described herein, further comprising a test window configured to allow observation of the test results.

A further embodiment of the invention relates to the device as described herein, wherein the detection reagents are chemically conjugated to the detectable marker to form a permanent, irreversible reagent-marker complex.

A further embodiment of the invention relates to the as described herein, wherein the detectable marker conjugated to the detection reagent is configured to be visible to a user when the sample is positive for Mx-B and/or CRP and/or PCT and/or BPI and.

A further embodiment of the invention relates to the device as described herein, wherein the device is configured to/or PCT and/or BPI in human blood samples.

One embodiment of the invention relates to a method for discriminating between bacterial and viral infection in a subject, comprising the steps of:
a. providing a sample from said subject,
b. providing the test system as described herein,
c. applying the sample to the test system,
d. observing the absence or presence of the detectable reagent-marker complex to determine whether the sample contains Mx-B and/or CRP and/or PCT and/or BPI, and
e. determining the infection status of the patient.

One embodiment of the invention relates to the method as described herein, wherein
a. the presence of Mx-B and the absence and/or low detection of CRP/PCT/BPI is indicative for a viral infection,
b. the absence of Mx-B and the presence of CRP/PCT/BPI is indicative for a bacterial infection; and
c. the presence of Mx-B and the presence of CRP/PCT/BPI is indicative for a mixed infection.

A further embodiment of the invention relates to the method as described herein, further observing the absence or presence of the detectable reagent-marker complex to determine whether the sample contains CRP/PCT/BPI.

One embodiment of the invention relates to the method as described herein, wherein
a. the presence of Mx-B and the absence of CRP/PCT and BPI is indicative for a viral infection,
b. the absence of Mx-B and the presence of CRP/PCT and BPI is indicative for a bacterial infection; and
c. the presence of Mx-B and the presence of CRP/PCT and BPI is indicative for a mixed infection.

A further embodiment of the invention relates to the method as described herein, wherein the sample is a blood sample.

A further embodiment of the invention relates to the method as described herein, wherein the presence of Mx-B, CRP/PCT and/or BPI is visible to the naked eye.

BRIEF DESCRIPTION OF DRAWINGS

FIG. 2 shows the results for different viral and bacterial pathogens.

DESCRIPTION OF EMBODIMENTS

Figure 1:
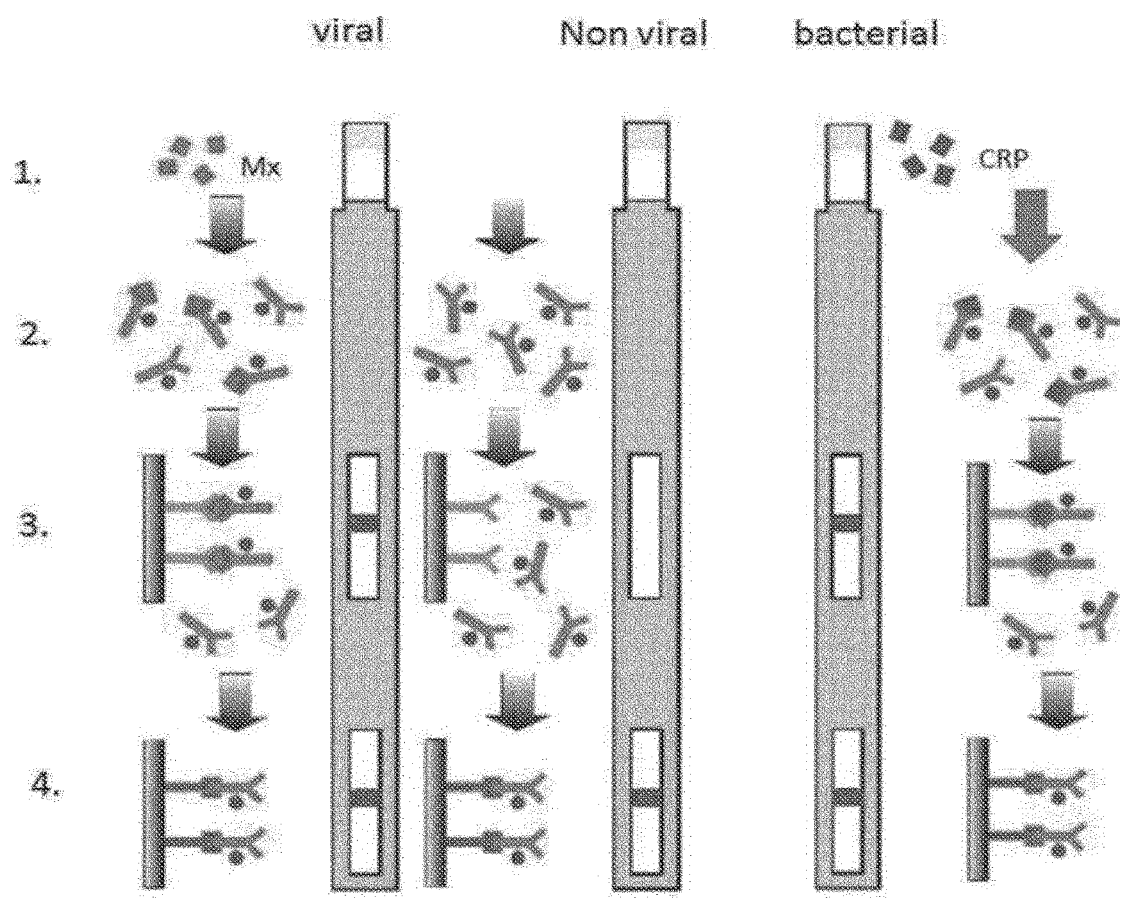
FIG. 1A depicts an exemplary test set up consisting of three test strips coated with labelled antibodies.
FIG. 1B depicts the different test pictures for viral infections, bacterial infection, mixed infections, or doubtful infection.
Figure 1B:
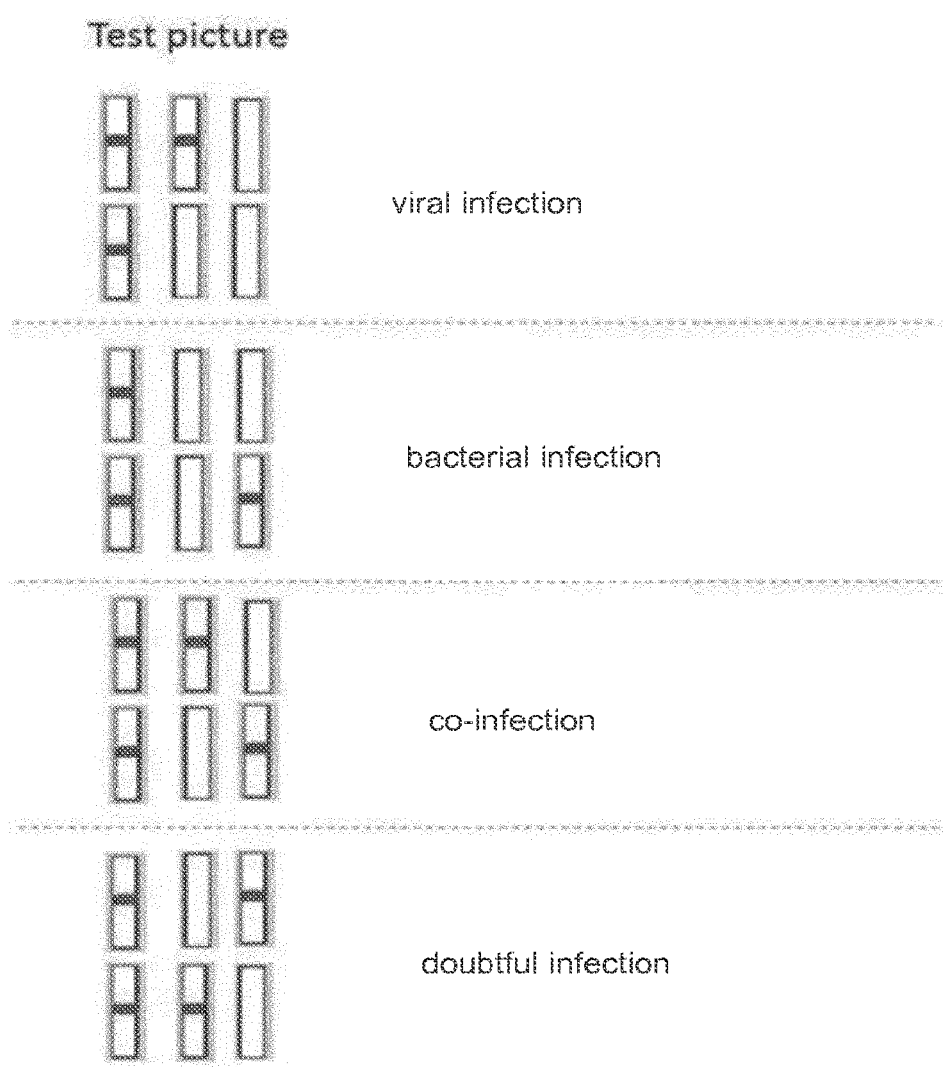

The present invention provides a point of care assay that is capable of differentiating viral and bacterial infections in short time. Specifically, there is provided a point of care diagnostic device comprising test markers for both viral and bacterial infection which effectively assists the medical doctor in the rapid differentiation of viral and bacterial infections. The point of care assay has the following advantages:
1.) This assay may dramatically reduce health care costs by limiting misdiagnosis and consequently over- and misuse of antibiotics.
2) The efficacy and ensurement of this assay is that the resistance against antibiotics will be reduced, because the antibiotics will be used only when a bacterial infection is present.
3) This assay will increase the diagnostic portfolio of doctor's office and pharmacists.

Thus, the present invention contributes use antibiotics appropriately. This means using antibiotics only when needed and, if needed, using them correctly.

Antibiotics do not fight infections caused by viruses like colds, flu, most sore throats, and bronchitis. Even many sinus and ear infections can get better without antibiotics. Instead, symptom relief might be the best treatment option for these infections. Taking antibiotics for viral infections, such as colds, flu, most sore throats, and bronchitis:

will not cure the infection;
will not keep other people from getting sick;
will not help you or your child feel better;
may cause unnecessary and harmful side effects; and
may contribute to antibiotic resistance, which is when bacteria are able to resist the effects of an antibiotic and continue to cause harm.

Incorrectly prescribed antibiotics have questionable therapeutic benefit and expose patients to potential complications of antibiotic therapy. The rapid result obtained from the point of care test thus permits a correct diagnosis and support the medical practitioner in his decision for prescribing the correct medication.

For the point of care assay different devices may be applicable, e.g., lateral flow immunoassay device or an optical sensor system, which is designed to interact with a mobile computer device as described in WO2016/116181.

Thus, according to one embodiment of the present invention a sample analysis device is used, for example a test strip, to determine if an infection is bacterial or viral. The test strip includes a sample application zone and a detection zone. In this method, a sample is collected, and transferred to the test strip. The detection zone includes at least one reagent specific to a bacterial marker and at least one reagent specific to a viral marker.

In one embodiment, the marker for viral infection is Mx-B and the marker for bacterial infection is C-reactive protein (CRP). High Mx-B protein levels are strongly correlated with systemic viral infection. The interferon-inducible myxovirus (Mx) proteins play important roles in combating a wide range of virus infections. Mx-homologous proteins inhibits RNA and DNA viruses.

Recently it was found that the Mx-B-protein is the important protein which transport viral components out of the cell [2]. For instance, the HIV-protein will be transported and eliminated by the Mx-B protein, and not by the Mx-A-protein [1]. Therefore, this point of care assay uses the Mx-B-protein, because it has only a 63% homology to the Mx-A protein, and is therefore the functional Mx-protein within the Mx GTPases family [3]. It was shown, that Mx-B strongly inhibits viral infections by reducing the level of integrated viral DNA. Furthermore, the Mx-B protein is located within the nucleus and the cytoplasma. In contrast, the Mx-A protein is only located in the cytoplasma [4]. Based on the new findings, Mx-B is selected by the inventors as a reliable marker for viral infections.

C-reactive protein (CRP), an acute phase protein produced by the liver in response to infection, is a reliable biomarker for bacterial infections. CRP levels in healthy individuals are considered less than 0.5 mg/L, and the CRP levels are elevated in infectious conditions.

Procalcitonin (PCT) is a polypeptide hormone with 116 amino acids. This protein will be mostly produced by the C-cells of the thyroid gland. Normally there is a very limit level of PCT in the blood. In contrast, during a bacterial Infection this protein will be expressed and found to be between 0.5 ng/ml and 2 ng/ml. The advantage of this protein is that it will be detected after 6 hours of infection, whereas the CRP will be detected in earliest time point of 12-16 hours.

According to one embodiment of the invention the present invention relates to a rapid screening test for identifying Mx-B and/or CRP/PCT/BPI in a patient sample. The sample may be, for example peripheral blood sample, nasopharyngeal aspirates, tears, spinal fluid, and middle ear aspirates.

The bactericidal/permeability-increasing protein (BPI) is a pluripotent protein located in neutrophils and tissue that likely plays a pivotal role in host defense against Gram-negative bacteria and their endotoxin by means of its antibiotic and endotoxin neutralizing and -disposing functions. BPI is considered as additional biological marker for the improved point of care test in order to improve the reliability and accuracy of the test. During a bacterial Infection this protein will be expressed and found to be between 1 μg/ml and 20 μg/ml.

Thus, a further embodiment of the invention relates to the point of care test for identifying Mx-B, BPI, and/or CRP/PCT in a patient sample.

According to one embodiment of the invention the detection zone includes at least one reagent with binding affinity to the viral marker Mx-B and at least one reagent with binding affinity to the bacterial marker CRP/PCT and optionally at least one reagent with binding affinity to BPI such that, when the markers present in the sample contact the respective reagents, a labeled complex form. The detection zone includes a bacterial marker binding partner which binds to the first labeled complex and a viral marker binding partner which binds to the second labeled complex. The sample is then analyzed for the presence of the viral marker and/or the bacterial marker.

The detection zone may be functionalized by immobilizing various receptor molecules which specifically bind to the respective markers. The receptor molecules may be selected from natural origin, e.g. antibodies, antibody fragments or the like. The receptor molecules may be synthetically produced molecules, e.g., aptamers. The detection zone comprises at least one sensor region, on which, as receptors for sensing the respective markers, antibodies or other specificity imparting receptors, such as aptamers, which specifically bind to the respective markers to be detected, are arranged. Thus, an effective, easy to apply functionalization of the sensor region surface is achieved.

The antibodies or other specificity imparting receptors such e.g. aptamers have a high selectivity for detecting specific analytes; therefore, they are particularly suitable for recognizing specific disease markers. In relation to possible receptors, the antibodies arranged on the sensor surface or other specificity imparting receptors such as aptamers e, g. bind the analyte to be detected and, in the process, lead to a change in the properties. In some embodiments, the aptamers are advantageous in that they are more stable and therefore permanently functional.

As aptamers share similar applications to antibodies, numerous detection methods that take advantage of antibodies can be developed into aptamer-based methods. For instance, most immunoassays for small molecules are competitive assays relying on the replacement of surface-bound antibodies by the analyte in solution.

One embodiment of a device of the present invention includes a sample application zone.

A further embodiment of the invention relates to the device which additionally includes a reagent zone. The reagent zone comprises at least one reagent specific to the viral bacterial marker such that, when a viral marker present in the sample contacts said reagent, a labeled viral reagent complex forms. Further, the reagent zone comprises at least one reagent specific to the bacterial marker such that, when a bacterial marker present in the sample contacts said reagent, a labeled bacterial reagent complex forms. In one embodiment of the invention the reagent zone comprises one reagent specific to the bacterial marker CRP/PCT and one reagent specific to the bacterial marker BPI, such that, when said bacterial markers present in the sample contact said reagents, labeled complexes are formed.

The detection zone on the device includes a viral marker binding partner which binds to the labeled viral reagent complex and a bacterial marker binding partner which binds to the labeled bacterial reagent complex. The device could be a chromatography test strip.

In a preferred embodiment, the presence of the viral marker or the bacterial marker is indicated by a test line visible to the naked eye. The presence of the viral marker may be indicated by a first test line while the presence of the bacterial marker is indicated by a second and/or third test line. In some embodiments, the first test line displays a first color when positive and the second test line displays a second color different from the first color when positive, and/or the third test line displays a third color different from the first and second color when positive. In embodiments where the first, the second and the third test line are located in the same space on the sample analysis device, it is advantageous having different colors formed when the first, the second, and/or third test line are positive.

In one embodiment, the two or three test lines are spatially separate from each other on the device. In such an embodiment, the color may be the same when the test lines are positive.

In one embodiment of the invention, the sample to be analyzed is applied to a carrier. The carrier can be made of one single chromatographic material, or preferably several capillary active materials made of the same or different materials and fixed on a carrier backing. These materials are in close contact with each other so as to form a transport path along which a liquid driven by capillary forces flows from an application zone, passing the reagent zone, towards one or more detection zones and.

Preferably, the sample is directly applied to the carrier by dipping the carrier's application zone into the sample. Alternatively, application of the sample to the carrier may be carried out by collecting the sample with a dry or wetted wiping element from which the sample can be transferred, optionally after moistening, to the carrier's application zone. Usually, the wiping element is sterile and may be dry or pretreated with a fluid before the collection step. Materials suitable for wiping elements according to the invention may comprise synthetic materials, woven fabrics or fibrous webs.

Depending on the type of detection method, different reagents are present in the reagent zone, which is located between the application zone and the detection zone. In a sandwich immunoassay, it is preferred to have a labeled, non-immobilized reagent in the reagent zone that is specific to the viral and bacterial marker to be detected. Thus, when a viral or bacterial marker present in the sample contacts the corresponding labeled viral or bacterial reagent present in the reagent zone, a labeled complex is formed between the marker and the corresponding labeled reagent. The labeled complex in turn is capable of forming a further complex with an immobilized viral or bacterial marker binding partner in the detection zone. In a competitive immunoassay, the reagent zone preferably contains a labeled, non-immobilized marker analogue which competes with the marker for the immobilized marker binding partner in the detection zone. The marker binding partners in the reagent zone and in the detection zone are preferably monoclonal, polyclonal or recombinant antibodies or fragments of antibodies capable of specific binding to the corresponding marker.

Detection of the marker may be achieved in the detection zone. The immobilized molecule binds the labeled complex or the labeled marker-analogue by immune reaction or other reaction in the detection zone, thus building up a visible test line in the detection zone during the process. Preferably, the label is an optically detectable label. Forming a complex at the detection zone immobilizes the label and the test line becomes visible for the naked eye, indicating a positive test result. Suitable are direct labels, e.g. particularly gold labels which can be best recognized by the naked eye. Additionally, an electronically read out device (e.g. on the basis of a photometrical, acoustic, impedimetric, potentiometric and/or amperometric transducer) can be used to obtain more precise results and a semi-quantification of the analyte. Other suitable labels may be latex, fluorophores or phosphorophores.

In one embodiment, the sensitivity of visually read lateral flow immunoassay tests is enhanced by adding a small quantity of fluorescing dye or fluorescing latex bead conjugates to the initial conjugate material. When the visible spectrum test line is visibly present, the test result is observed and recorded.

In one embodiment of the invention, the reagents are configured such that the visible test line corresponding to the presence of the viral marker will be separate from the test lines corresponding to the presence of the bacterial markers. Therefore, it can be readily determined whether the sample contained bacterial or viral markers (or both) simply by the location of the development of the test lines in the detection zone. In another preferred embodiment, the reagents may be chosen such that differently colored test lines are developed. That is, the presence of a viral marker will cause the development of a differently colored line than that developed by the presence of a bacterial marker. For example, the label corresponding to the reagent recognizing the viral marker may be red, whereas the label corresponding to the reagent recognizing the bacterial markers may be green. Differently colored labels that may be attached to the non-immobilized reagents are well known. Some examples include, but are not limited to, colloidal gold, colloidal selenium, colloidal carbon, latex beads, paramagnetic beads, fluorescent and chemiluminescent and mixtures thereof.

FIG. 1 show a chromatography test strip with a test line corresponding to the presence of a viral marker, a second, separate test line that detects the presence of a first bacterial marker and a third, separate test line that detects the presence of a second bacterial marker. The sample is applied to the application zone of the test strip. As shown in FIG. 1, the sample then passes a reagent zone containing at least one labeled viral binding partner and at least one labeled bacterial binding partner. The labeled viral binding partner is capable of specifically binding to a viral marker of interest to form a conjugate which in turn is capable of specifically binding to another specific reagent or binding partner in the detection zone. The labeled bacterial binding partner is capable of specifically binding to a bacterial marker of interest to form a conjugate which in turn is capable of specifically binding to another specific reagent or binding partner in the detection zone.

The test strip also includes a detection zone containing at least one first section for detection of a viral marker, e.g. a test line, including an immobilized specific binding partner, complementary to the viral reagent complex formed by the viral marker and its labeled binding partner. Thus, at the test line, detection zone binding partners trap the labeled viral binding partners from the reagent zone along with their bound viral markers. This localization of the viral marker with its labeled binding partners gives rise to an indication at the test line. At the test line, the presence of the viral marker is determined by qualitative and/or quantitative readout of the test line indication resulting from the accumulation of labeled binding partners.

The detection zone also includes at least one section for detection of at least one bacterial marker, e.g. a test line, including an immobilized specific binding partner, complementary to the bacterial reagent complex formed by the bacterial marker and its labeled binding partner. Thus, at the test line, detection zone binding partners trap the labeled bacterial binding partners from the reagent zone along with their bound bacterial markers. This localization of the bacterial marker with its labeled binding partners gives rise to an indication at the test line. At the test line, the presence of the bacterial marker is determined by qualitative and/or quantitative readout of the test line indication resulting from the accumulation of labeled binding partners In one embodiment of the invention the detection zone may contain a further test line to detect a second bacterial marker.

One example of a point of care test for distinguishing viral and bacterial infection is shown in FIG. 1. As discussed above, Mx-B is a diagnostic marker for viral infection, while CRP and BPI are diagnostic markers for bacterial infection. A positive result for the Mx-B protein, with a negative result for the CRP/PCT and BPI protein indicates a viral infection. A positive result for the CRP/PCT and BPI with a negative result for the Mx-B protein indicates a bacterial infection. A weak positive result for Mx-B, CRP/PCT and BPI indicates an infection with both a bacterium and a virus (co-infection). No bacterial or viral infection is indicated by a negative result for Mx-B, CRP/PCT and BPI. While particular color lines are discussed in this example, other colors, or the same colors at different locations on the test strip to indicate viral or bacterial markers, are within the spirit of the present invention.

When development of different colored lines is utilized, the lines may or may not be separated by space. In the latter instance, the labels are chosen such that the color seen when both markers are present is different from the colors seen when the individual markers are present. For example, the presence of the viral marker may be indicated by a red line; the presence of the bacterial marker by a blue line; and the presence of both by a purple line (combined red and blue).

In another embodiment, the test strip may also include a control section which indicates the functionality of the test strip. If present, the control section can be designed to convey a signal to the user that the device has worked. For example, the control section may contain a reagent (e.g., an antibody) that will bind to the labeled reagents from the reagent zone. As a further alternative, the control section could contain immobilized viral and bacterial markers which will react with excess labeled reagent from the reagent zone. The control section may be located upstream or downstream from the detection zone. A positive control indicator tells the user that the sample has permeated the required distance through the test device.

Mx homologues could also be detected in about 10% of bacterial infection associated with fever. In order to enhance the reliability of the test the cut-off for Mx-B protein is set to be in the range of 0.01-0.05 U/10,000 leucocytes, preferably is 0.025 U/10,000 leucocytes. For CRP, the cut-off is set to be in the range of 5-100 mg/L, or in the range of 25-75 mg/L, or is 40 mg/L. For PCT the cut off is set to be in the range of 0.5 ng/ml to >2 ng/ml. For BPI the cut off is set to be in the range of 1 µg/ml to >10 µg/ml.

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

Example 1—Description of Assay

The Point of Care Assay is performed with a lateral Flow Device. The appropriate reagents needed for each assay are already included in the Cartridge.

Step A: Due to adhesive force a drop of blood (approx. 0.005 ml-0.010 ml) is transferred von the Cartridge into the device.

Step B: First of all, the cells in the blood drop are lysed with approx. 0.001 ml lysis buffer which consists of (20% NP-40, 100 mM Tris-HCL, ph 7.2, 0.05 sodium azide).

Step C: The lysed blood is directed above two test strips and therefore incubated.

Step D: Antibody solution 1 against Mx-B binds possible available Mx-B protein in the blood. This antibody is already conjugated with a labeled marker.

Step D: The bound Mx-B protein will be directed over a second carrier solution, in which a second antibody against Mx-B is located. Only already bound Mx-B protein with the first labeled antibody will be bound from the second antibody.

Step E: After rinsing the carrier solution the first labeled and bound antibody is made visible in form of a color reaction on the strip.

Step F: The detection of CRP/PCT/BPI is performed as described in step A to step E, whereas one antibody against CRP/PCT and one antibody against BPI is used on the second test strip.

Example 2—Test Procedure

In two different ambulances, patients of unknown origin were tested for Mx-A protein, Mx-B protein, CRP/PCT and BPI from whole blood. All patients signed a declaration of consent under the Helsinki Agreement that their data are intended solely for research. 113/5000. Subsequently, the anamnesis was continued in the course of the investigations and the origin of the infection was determined. Thus, 120 viral infections and 50 bacterial infections could be distinguished. The result of this investigation is documented in FIG. 2. With the help of the Mx-B protein, 92% of the viral infections were detected. In contrast, only 77% of the identical viral diseases were detected using the Mx-A protein. With the help of the determination proteins CRP/PCT/BPI, the spectrum for the detection of bacterial diseases was increased to 90%. If only the CRP and PCT protein had been measured, only 80% of the bacterial diseases would have been detected. Thus, the combination of the markers Mx-B protein for viral diseases and CRP/PCT/BPI for bacterial diseases results in a sensitivity or specificity detection of over 90%.

Example 3—Results

Description of the results from a viral infection: To prove that the color reaction is functioning, both test strips on the left side are controls. The middle strip on the top colors, the strip below remains colorless. Both strips on the right side remain colorless.

Description of the results from a bacterial infection:
Both strips in the middle remain colorless, the one on the top as well but the right strip below colors.

Description of the results from a mixed infection: The middle strip on the top colors and as well the strip below.

REFERENCES

[1] Haller, O, Dynamins are forever Mx-B inhibits HIV-1. Cell Host Microbe. 2013 Oct. 16; 14(4):371-3.
[2] Wei W., et al., Accumulation of Mx-B/Mx2-resistant HIV-1 Capsid Variants During Expansion of the HIV-1 Epidemic in human populations. EBioMedicine. 2016 June; 8: 230-236.
[3] Melen, K., et al., Human Mx-B protein, an interferon-alpha inducible GTPase, contains a nuclear targeting signal and is localized in the heterochromatin-region beneath the nuclear envelope. J Biol Chem. 1996 Sep. 20; 271(38):23478-86.
[4] Gao, S., et al., Structural basis of oligomerization in the stalk region of dynamin-like Mx-A. Nature. 2010 May 27; 465(7297):502-6.
[5] Wussow, P.v., et al., Humoral response to recombinant IFN-α 2b in patients receiving recombinant IFN-α therapy. J Interferon Res. 1989 September; 9 Suppl 1: S25-31
[6] Jakschies, D., et al., Emergence and decay of the human MX homolog in mononuclear cells from cancer patients during and after IFN-α therapy. J Biol Response Mod. 1990 June; 9(3):305-12.
[7] Wussow, P.v., et al., The interferon-induced MX-homologous protein in patients with symptomatic HIV-1-infection. AIDS. 1990 February; 4(2):119-24.
[8] Wussow, P.v., et al., The human MX-homologous protein is specifically induced by type-1-IFNs. Eur. J. Immunology. 1990 September; 20(9), 2015-2019.
[9] Jakschies D., et al., Correlation of the antiproliferative effect and the Mx-homologous protein induction by IFNs in patients with malignant melanoma. J Invest Dermatol. 1990 December; 95(6 Suppl):238S-241S.
[10] Wussow, P.v., et al., Effective natural interferon-alpha therapy in recombinant interferon-alpha-resistant patients with hairy cell leukemia. Blood. 1991 Jul. 1; 78(1):38-43.
[11] Wussow, P.v., et al., Treatment of anti RIFN-α-2 antibody positive CML-patients with natural IFN-α. Br J Haematol. 1991 June; 78(2):210-6.
[12] Jakschies, D., et al., The human IFN-induced Mx-homologous proteins identified by 2D SDS-PAGE is specifically induced by type-1-interferons. (1991). Proc. Int. Meeting on 2-D-Electrophoresis London, 16.18.7.1991: 163.
[13] Towbin, H., et al., A whole blood immunoassay for the interferon-inducible human Mx-protein. J Interferon Res. 1992 April; 12(2):67-74.
[14] Jakschies, D., et al., Strong transient expression of the interferon-induced Mx-A-protein in hepatitis A, but not in acute hepatitis B and C. Hepatology. 1994 April; 19(4): 857-65.
[15] Rump, J. A., et al., Common variable immunodeficiency (CVID) and Mx-A-protein expression in blood leucocytes. Clin Exp Immunol. 1995 July; 101(1):89-93.
[16] Al-Masri, A., et al., Intracellular staining of Mx proteins in cells from peripheral blood, bone marrow and skin. Mol Pathol. 1997 February; 50(1):9-14.
[17] Self W. H., et al., Diagnostic Accuracy of FebriDx: A Rapid Test to Detect Immune Responses to Viral and Bacterial Upper Respiratory Infections. J Clin Med. 2017 Oct. 7; 6(10).

The invention claimed is:

1. A method for discriminating between a bacterial infection and a viral infection in a subject, the method comprising the steps of:
(a) providing a sample from the subject;
(b) providing a point-of-care assay device comprising:
(i) a sample application zone;
(ii) a detection zone with detection reagents consisting of a first detection reagent with binding affinity to Mx-B-protein (Mx-B), a second detection reagent with binding affinity to C-reactive Protein (CRP), a third detection reagent with binding affinity to procalcitonin (PCT), and a fourth detection reagent with binding affinity to bactericidal/permeability-increasing protein (BPI); and
(iii) a test window configured to allow observation of the test results;
(c) applying the sample to the sample application zone of the assay device;
(d) observing the absence or presence of detectable reagent-marker complexes in the test window of the assay device to determine whether the sample contains Mx-B, CRP, PCT, and/or BPI; and
(e) determining the infection status of the subject,
wherein the patient is determined to have a viral infection when (i) Mx-B is present and (ii) CRP, PCT, and BPI are absent;
wherein the patient is determined to have a bacterial infection when (i) Mx-B is absent, (ii) CRP and/or PCT is present, and (iii) BPI is present;
wherein the patient is determined to have a mixed viral and bacterial infection when (i) Mx-B is present and (ii) CRP, PCT, or BPI are present.

2. The method of claim 1, wherein the sample is a blood sample.

3. The method of claim 1, wherein the presence or absence of Mx-B, CRP, PCT, and BPI is visible to the naked eye.

4. The method of claim 1, wherein said detection reagents are selected from the group consisting of synthetic molecules, nucleotides, nucleic acids, aptamers, peptides, proteins, enzymes, and antibodies.

5. The method of claim 4, wherein said detection reagents are labelled with a detectable marker.

6. The method of claim 5, wherein the detectable marker is selected from the group consisting of an enzyme label, fluorescent label, radiolabel, particulate label, colored latex particle, colored plastic particle, a colored phosphor particle, and a fluorescent particle.

7. The method of claim 1, wherein the detection reagents are chemically conjugated to the detectable marker to form a permanent, irreversible reagent-marker complex.

8. The method of claim 1, wherein the detectable marker conjugated to the detection reagent is configured to be visible to a user when the sample is positive for Mx-B and/or CRP and/or PCT and/or BPI.

9. The method of claim 1, wherein the device is configured to qualitatively and/or quantitatively measure the presence of Mx-B and/or CRP and/or PCT and/or BPI in human blood samples.

* * * * *